United States Patent [19]

Gago et al.

[11] 4,346,081

[45] Aug. 24, 1982

[54] COMPOSITIONS FOR INGESTION BY RUMINANTS TO REMOVE PROTOZOA, PROCESS FOR THEIR PREPARATION AND USE OF THESE COMPOSITIONS FOR THE FEEDING OF RUMINANTS

[75] Inventors: Ignace Gago, Braine-l'Alleud; Guillaume Coppens, Brussels, both of Belgium

[73] Assignee: Interox (Société Anonyme), Brussels, Belgium

[21] Appl. No.: 223,775

[22] Filed: Jan. 9, 1981

[30] Foreign Application Priority Data

Jan. 11, 1980 [FR] France .................................. 80 00774

[51] Int. Cl.$^3$ ............................................... A61K 33/40
[52] U.S. Cl. ..................................................... 424/130
[58] Field of Search .......................................... 424/130

[56] References Cited

U.S. PATENT DOCUMENTS

| | | | |
|---|---|---|---|
| 2,304,098 | 12/1942 | Jones et al. | 424/130 |
| 2,429,971 | 10/1947 | Young | 424/130 |
| 2,970,915 | 2/1961 | Ferrari | 426/22 |
| 2,978,330 | 4/1961 | Ferrari | 426/26 |
| 3,531,294 | 9/1970 | Glabau | 426/22 |

FOREIGN PATENT DOCUMENTS 2319304 2/1977 France .
2345940 10/1977 France .

OTHER PUBLICATIONS

Krivopishin et al., Chem. Abst. vol. 89 (1978) p. 22747p.
Haase, Chem. Abst. vol. 45 (1951) p. 2148e.

*Primary Examiner*—Sam Rosen
*Attorney, Agent, or Firm*—Spencer & Kaye

[57] ABSTRACT

A composition for ingestion by ruminants to remove protozoa contains a peroxide of a metal of group 2 of the Periodic Table.

10 Claims, 3 Drawing Figures

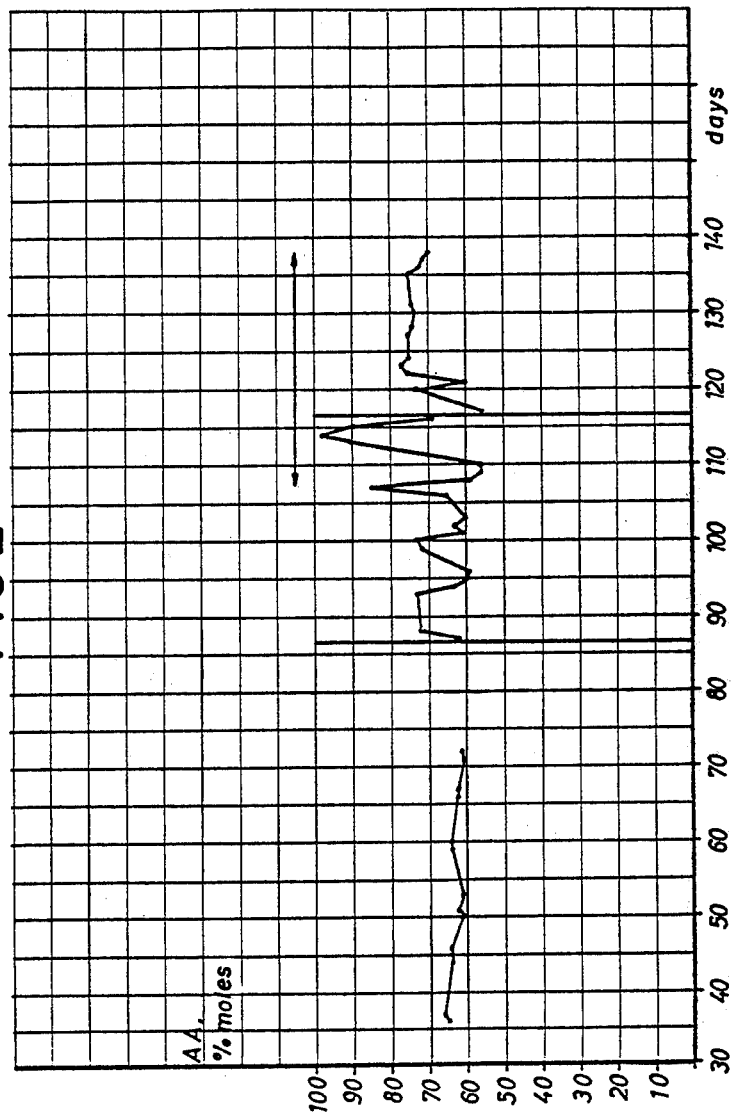

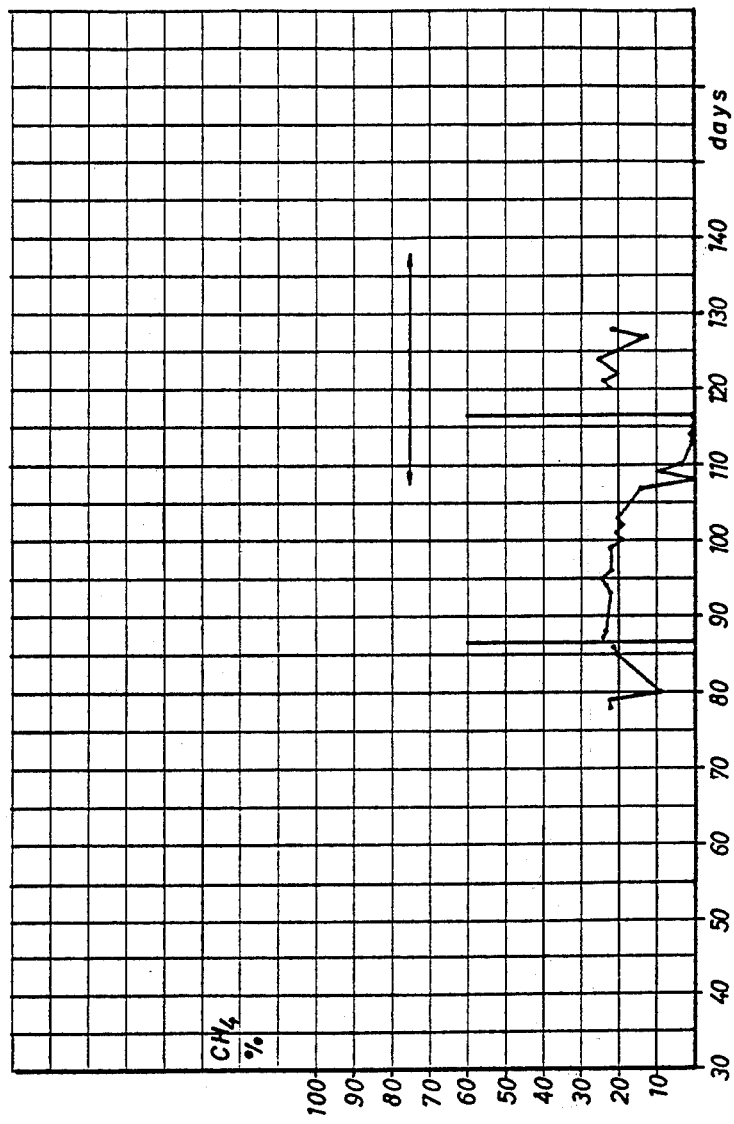

COMPOSITIONS FOR INGESTION BY RUMINANTS TO REMOVE PROTOZOA, PROCESS FOR THEIR PREPARATION AND USE OF THESE COMPOSITIONS FOR THE FEEDING OF RUMINANTS

BACKGROUND OF THE INVENTION

The invention relates to compositions for ingestion by ruminants, such as foodstuff compositions or compositions for veterinary or prophylactic use. It also relates to a process for the preparation of such compositions and the use of these compositions for the feeding of ruminants.

Ruminants are capable of synthesising the aminoacids which are essential for building the proteins of the organism from carbohydrates, such as cellulose, the hemicelluloses, starch and soluble sugars, and from nitrogen-containing foodstuffs which are not proteins, such as urea and certain ammonium salts. During digestion, the carbohydrates are largely degraded in the rumen by various types of specific bacterial enzymes, to give intermediate products (cellobiose, maltose, glucose, xylose, uronic acids and the like), whose nature depends on that of the starting carbohydrates. These products are subsequently converted, by other bacteria, into final products, including short-chain volatile fatty acids such as acetic acid. The energy provided by the carbohydrates in particular allows the flora of the rumen to produce microbial proteins, inter alia with the ammonia liberated by bacterial hydrolysis of the nitrogen-containing substances.

The conversion of the carbohydrates is accompanied by the formation of waste products such as methane. Abnormally high proportions of this product lead to high losses of energy.

If the rumen is contaminated with protozoa, which contamination can, for example, result from the ingestion of contaminated drinking water or contaminated forage or from contact with infected animals, a reduction in the formation of acetic acid in the rumen is observed.

Moreover, a reduction in the efficiency of the synthesis of the bacterial proteins in the rumen is observed. To compensate this reduction in yield, it is necessary to complement the feed of the ruminants by means of protein substances such as oilseed cakes, cereals and edible flours, of which a part could be used for direct human nutrition. This runs counter to all the efforts made to increase human foodstuff resources.

The destruction of the protozoa present in the rumen, so as to improve the synthesis of proteins, is furthermore very difficult. In fact, it requires the selection of a fauna-removing agent, which is capable of destroying the protozoa present in the rumen without at the same time destroying the other micro-organisms, necessary for normal digestion. Furthermore, it is necessary that this fauna-removing agent should not be toxic to the animal.

SUMMARY OF THE INVENTION

The present invention proposes to provide compositions for ingestion by ruminants, which have a fauna-removing effect towards protozoa, do not destroy the micro-organisms present in the rumen and necessary for digestion, lead to an improvement in the assimilation of the ingested nitrogen-containing non-protein materials and of the ingested carbohydrates by the ruminants, and, finally, are non-toxic. These compositions make it possible to feed the ruminants with rations which contain more nitrogen-containing non-protein materials and less proteins, or to increase production. Furthermore, they reduce the generation of methane in the rumen.

To achieve this object, the invention provides compositions, for ingestion by ruminants, which contain a peroxide of a metal of group 2 of the Periodic Table.

DETAILED DESCRIPTION OF THE INVENTION

Figure 1:
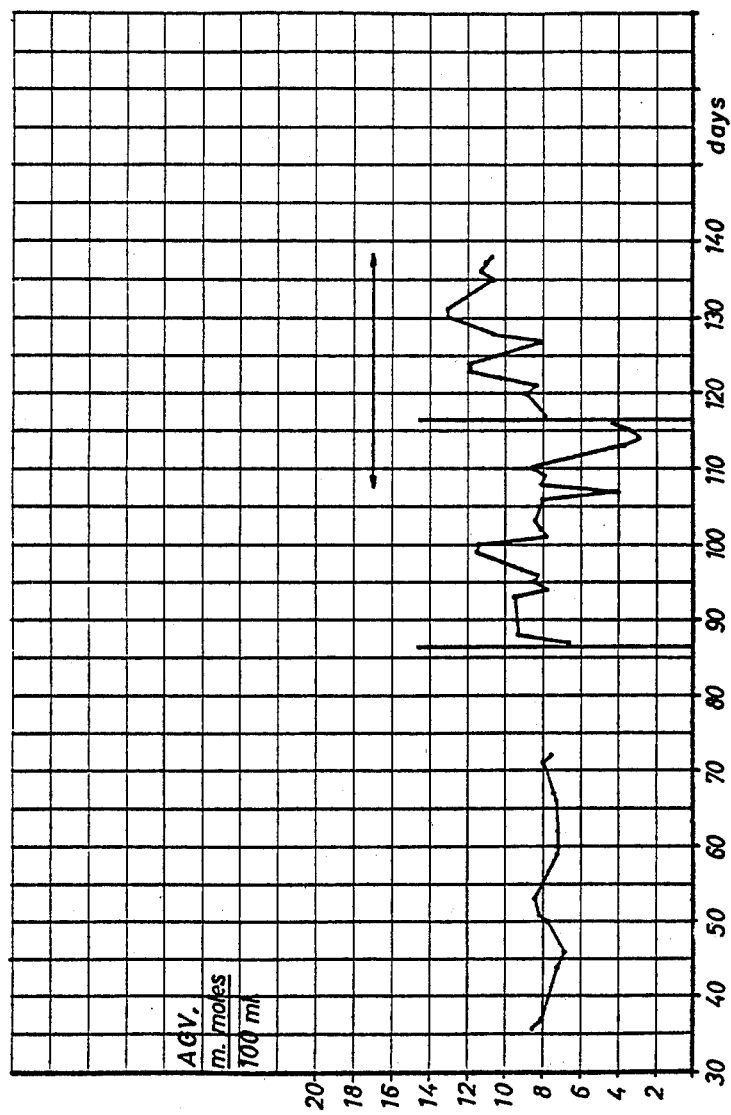

The peroxide of a metal of group 2 is in general chosen from amongst the peroxides of calcium, magnesium, zinc or strontium, and their mixtures. The peroxides of calcium and of magnesium are particularly preferred. Good results have been obtained with calcium peroxide.

The peroxide of a metal of group 2 which is employed can be of any known quality. Where the material is calcium peroxide, a commercial product containing from 30 to 90% of calcium peroxide is generally used, the remainder consisting in particular of calcium oxide and calcium hydroxide and possibly a calcium salt and water. Calcium peroxide of a different quality to this can also be used.

The peroxide of a metal of group 2 can be employed in greatly varying amounts. In general, it is introduced into the compositions according to the invention in such proportions that the ration ingested daily, calculated as active oxygen relative to the weight of the animal, is greater than 0.00005% and most commonly greater than 0.0001%. In general, these proportions are such that the ration of peroxide ingested daily does not exceed 0.06% and most commonly does not exceed 0.04% (calculated as active oxygen).

Preferably, the peroxide is introduced into the compositions according to the invention in such proportions that the ration ingested in one dose by the animal is between 0.0001 and 0.1% by weight of peroxide compound, in its actual form, relative to the weight of the animal. Good results have been obtained with ingestions corresponding to 0.001 to 0.05% by weight of peroxide relative to the weight of the animal. Other doses may also prove suitable.

The peroxide can be administered in a single dose or in several periodic doses. In general, for reasons of convenience and to avoid subsequent recontamination, the peroxide is administered periodically. The periodicity can vary and depends on the risk of contamination, the method of feeding, the amount of peroxide administered per ration, the other constituents of the composition and the presentation of the composition, and on the animals themselves (age, sex, physiological condition, race), and the like. Good results have been obtained by daily administration of rations of the composition according to the invention.

The compositions according to the invention can be in different forms. Thus they can be in the form of feeding compositions containing the peroxide and one or more feeds for ruminants, such as forage of all kinds and in any of its forms (green, dehydrated, agglomerated and the like), such as grass and other forage gramineae, forage cereals (barley, maize, oats, wheat, sorghum, soya or rye), leguminosae (horsebeans, lucerne, sainfoin and clover), roots, tubercles and their by-products (beets and beet pulp), cabbage, colza, sunflower, vegetable waste (dried leaves, stalks, cereal chaff, bran, maize cobs and bagasse), and starches, as well as oilseed cakes, syrups and nitrogen-containing feedstuffs, such as urea and its derivatives (biuret and ureides), and ammonium salts. Such feeding compositions can furthermore contain small amounts of other additives such as inorganic salts, vitamins, trace elements, fats, flavourings and binders. Where the ruminants are essentially fed with feeding compositions, the proportion of peroxide in this composition is in general between 0.05 and 20% and most commonly between 0.1 and 10% of the weight of ingested dry materials. Good results have been obtained by using feeding compositions containing between 0.2 and 5% by weight of peroxide. If the animals have other feed sources, the amount of peroxide in the feeding composition can be increased proportionately.

The feeding compositions according to the invention can be in various physical forms, for example in compacted or granulated forms, in the form of a powder or even in semi-liquid forms.

The compositions according to the invention can also be in the form of a complement to the normal feed. Thus, they can be in the form of prophylactic or veterinary compositions containing the peroxide, optionally with a carrier of the carbohydrate type (starchy materials, cellulosic materials and the like) digestible by the animals, and various other additives such as vitamins, inorganic salts, trace elements, emulsifiers, flavourings and binders, as well as certain active substances appropriate to the specific needs of the animal. These supplementary materials can be in various physical forms (powders, compacted or granulated solids or, optionally, semi-liquid forms) and can be given to the animals in the form of their ration separate from the feed. They can also advantageously be mixed, at the time of use, with the feeding rations. Such veterinary compositions can contain from 5 to 90%, and preferably from 10 to 60%, by weight of peroxide.

The compositions according to the invention can also be in the form of so-called lickstones (or nibbling stones). In this case, they can contain, in addition to the peroxide, various other additives such as vitamins, more particularly vitamins A, D, E and PP, trace elements (iron, copper, cobalt, manganese, zinc, selenium, tin and the like), nitrogen-containing non-protein materials (urea and the like), inorganic salts (chlorides, fluorides, iodides, carbonates, bicarbonates and phosphates of all types, whether neutral or acid, of metals of groups 1 and 2 of the Periodic Table), sulphur-containing materials (sulphur and sulphides), hydrocarbon carriers (containing starchy or cellulosic materials, such as flours and brans), such as those mentiond earlier as foodstuffs, flavourings, fats (tallow or coconut fat) and various other additives usually employed in lickstones or nibbling stones, in particular additives which can be as a binder or filler (magnesium sulphate, oxide and hydroxide, cements, gypsum, chalk, aluminum sulphate, alum and gelatin).

The compositions according to the invention, which are in the form of lickstones or nibbling stones, can contain varying amounts of peroxide. In general they contain from 2 to 60%, preferably from 5 to 50%, by weight of peroxide.

Thus, very suitable compositions, according to the invention, for lickstones contain:
from 2 to 60% by weight of peroxide,
from 0.1 to 40% by weight of inorganic salts,
from 0.1 to 60% by weight of nitrogen-containing materials,
from 0.1 to 20% by weight of carbohydrate carriers,
from 0.1 to 10% by weight of a mixture based on trace elements and vitamins,
from 0.5 to 30% by weight of flavourings,
from 0 to 5% by weight of fats,
from 0 to 5% by weight of sulphur-containing materials and
from 0 to 10% by weight of other additives usually employed in lickstones or nibbling stones.

The invention also relates to a process for the preparation of feeding compositions for ingestion by ruminants, the compositions being in the form of lickstones, according to which (a) a dry homogeneous mixture is prepared, which contains a metal of group 2 of the Periodic Table and at least one other constituent, which is insoluble or sparingly soluble in water, chosen from amongst carbohydrate carriers, fats, mixtures based on trace elements and vitamins, sulphur-containing materials and inorganic salts, nitrogen-containing materials and other additives which are insoluble or sparingly soluble in water;

(b) an aqueous solution containing at least one constituent chosen from amongst flavourings, inorganic salts, nitrogen-containing materials and other water-soluble additives is prepared;

(c) the aqueous solution is added to the homogeneous dry mixture, whilst kneading, so as to give a paste; and (d) the paste is dried.

By constituents which are insoluble or sparingly soluble in water, there are meant constituents whose solubility in water is less than the dose employed relative to the amount of water employed to produce the lickstone. The amount of water employed in the preparation of the aqueous solution can vary within wide limits. In general, to reduce the drying work, it is preferred to use amounts of water which do not exceed the dry weight of the lickstones or nibbling stones produced, and which preferably do not exceed 50% of this weight.

The paste obtained by kneading the homogeneous dry mixture and the aqeuous solution can optionally be moulded before being dried.

Drying can be carried out in accordance with any technique which is in itself known, for example by air drying at ambient temperature, or by drying with forced air circulation at varying temperatures which are in general between ambient temperature and 80° C.

An advantageous process consists in:

(a) homogeneously dry-mixing the peroxide with the carbohydrate carriers, the mixture based on trace elements and vitamins, the inorganic salts and nitrogen-containing materials which are sparingly soluble or insoluble in water, and any fats which may be used, any sulphur-containing materials which may be used and the other sparingly soluble or insoluble additives which may be used, (b) dissolving the flavourings, the inorganic salts and the water-soluble nitrogen-containing materials, as well as any other soluble additives which may be used, in water, (c) adding the aqueous solution to the dry mixture, whilst kneading, so as to give a paste which is moulded, and (d) drying the moulded paste.

The invention also relates to the use of the compositions for ingestion by ruminants, described above, for the feeding of ruminants, in which use compositions of the said type, furthermore containing at least one feedstuff, are orally administered to the ruminants.

A particular process consists in administering to the animal compositions which are such that the ration of peroxide ingested, calculated as active oxygen relative to the weight of the animal, varies from 0.00005 to 0.6% and preferably from 0.0001 to 0.4%.

This composition can advantageously be administered daily for any desired period and even throughout the total lifetime of the animal.

A particularly advantageous process consists in administering to the animal compositions which are so chosen that the ration of peroxide ingested varies with time. Thus, at the start of the treatment, it is advantageously possible to administer to the animal compositions which are such that the daily ration of peroxide, calculated as active oxygen, is relatively high, in general from 0.0005 to 0.06% of the weight of the animal, until the fauna has been removed, and then to maintain the fauna-free state by administration of reduced rations of peroxide, in general from 0.00005 to 0.002%.

In order to illustrate the invention, without thereby limiting its scope, practical examples of how it may be carried into effect are given below.

EXAMPLE 1

The biological effect of the fauna-removing agent (calcium peroxide) was determined using a sheep fitted with a fistula into the rumen.

The sheep, initially weighing about 70 kg, was given, twice daily, a feed ration consisting of 200 g of hay and 400 g of pulp pellets containing the equivalent of about 14% of crude proteins (half in the form of urea and half in the form of vegetable proteins), relative to the weight of dry material. The experiment extended over 138 days.

Starting on the 52nd day of feeding, an aqueous suspension of calcium peroxide was infused through the rumen fistula, twice daily, at the time at which the animal was consuming its feed ration.

The total daily doses were gradually increased up to the 116th day of feeding. Thereafter, all infusion of calcium peroxide was stopped. The injected doses are shown in Table 1 below.

TABLE 1

| Period | Daily dose of calcium peroxide (containing 80% of CaO$_2$) injected, g |
|---|---|
| 1st to 87th day | 0 |
| 88th to 94th day | 1.26 |
| 95th to 98th day | 3.16 |
| 99th to 101st day | 6.32 |
| 102nd to 106th day | 12.64 |
| 107th to 112th day | 18.96 |
| 113th to 116th day | 31.6 |
| 117th to 138th day | 0 |

During the experiment, samples of the contents of the rumen were taken regularly (from the 36th to the 138th day) and the gases in the rumen were determined (from the 44th to the 128th day) by the techniques described in the article by D. Demeyer and C. Van Nevel, Revue de l'Agriculture, 1978, 31 (6), pages 1093-1112.

From the 108th day onwards, complete disappearance of the protozoa was observed.

The volatile fatty acids (acetic acid, propionic acid, butyric acid, valeric acid and caproic acid) were determined, and the variation in the content thereof, expressed in millimols of volatile fatty acids (VFA) as a function of the time, expressed in days, is shown in FIG. 1. Examination of FIG. 1 shows that after injection of calcium peroxide the average content of volatile fatty acids has increased.

The variation in the content of acetic acid (AA), expressed in mol % of volatile fatty acids, as a function of the time expressed in days, is shown in FIG. 2. Examination of FIG. 2 shows that after injection of the calcium peroxide there was an increase in the average percentage of acetic acid in the volatile fatty acids.

The variation in the content of methane (CH$_4$), expressed in % of the gases in the rumen, as a function of the time expressed in days, is shown in FIG. 3. Examination of FIG. 3 shows a reduction in the percentage of methane in the gases during the injection of calcium peroxide.

EXAMPLE 2

A nibbling stone having the composition shown in Table 2 below is prepared:

TABLE 2

| Constituents | % by weight |
|---|---|
| calcium peroxide, containing 80% of CaO$_2$ | 12 |
| calcium hydrogen phosphate | 30 |
| Na$_2$CO$_3$ | 1.5 |
| wheat bran | 4 |
| urea | 20 |
| molasses | 22 |
| NaCl | 2 |
| wheat flour | 3.5 |
| mixture of trace elements and vitamins, trademark PROTECTOMIX, grade P 22, sold by PROTECTOR | 5 |

For this purpose, the calcium peroxide, calcium hydrogen phosphate, bran, wheat flour and mixture of trace elements and vitamins are dry-mixed homogeneously.

On the other hand, the molasses are dissolved hot in 3.84%, of their weight, of water, together with the sodium chloride and the sodium carbonate.

The solution is gradually added to the dry mixture, whilst kneading, until a paste is obtained. The paste is moulded and dried under ventilated conditions at 40° C.

This nibbling stone was consumed by 3 sheep at the rate of 47 to 122 g per day per animal. The appetency was very good.

We claim:

1. Composition for ingestion by ruminants and having a protozoa removing effect comprising an effective protozoa removing amount of a peroxide of a metal of group 2 of the Periodic Table in a ruminant feed.

2. Composition according to claim 1, wherein the peroxide comprises magnesium peroxide.

3. Composition according to claim 1, wherein the peroxide comprises calcium peroxide.

4. Composition according to claim 1, which contains from 0.2 to 5% by weight of peroxide.

5. Composition according to any one of claims 1 to 3, which furthermore contains at least one additive selected from the group consisting of vitamins, inorganic salts, trace elements, fats, flavourings, and binders.

6. Composition according to claim 5, which contains from 0.5 to 20% by weight of peroxide.

7. Composition for ingestion by ruminants and having a protozoa removing effect in the form of a lickstone, comprising an effective protozoa removing amount of a peroxide of a metal of group 2 of the Periodic Table and at least one additive selected from the group consisting of vitamins, trace elements, nitrogen-containing nonprotein materials, inorganic salts, sulphur-containing materials, carbohydrate carriers, flavourings and other additives usually employed in lickstones.

8. Composition according to claim 7, which contain from 5 to 50% by weight of peroxide.

9. Process for the preparation of a lickstone for ingestion by ruminants and having an effective amount of a protozoa removing agent comprising:
   (a) preparing a dry homogeneous mixture which contains a metal of group 2 of the Periodic Table as the protozoa removing agent and at least one other consitutuent, which is insoluble or sparingly soluble in water, selected from the group consisting of carbohydrate carriers, fats, mixtures based on trace elements and vitamins, sulphur-containing materials and inorganic salts, nitrogen-containing materials and other additives which are insoluble or sparingly soluble in water;
   (b) preparing an aqueous solution containing at least one constituent selected from the group consisting of flavourings, inorganic salts, nitrogen-containing materials and other water-soluble additives;
   (c) adding the aqueous solution to the homogeneous dry mixture, whilst kneading, so as to give a paste; and
   (d) drying the paste.

10. Process for feeding of ruminants, comprising administering orally to the ruminants a composition which contains an effective protozoa removing amount of a peroxide of a metal of group 2 of the Periodic Table and which additionally contains at least one foodstuff.

* * * * *